United States Patent
Jones et al.

(10) Patent No.: US 10,912,672 B1
(45) Date of Patent: Feb. 9, 2021

(54) ELECTRONICALLY REGULATED TEMPERATURE COMPRESSION BRACE

(71) Applicants: William Jones, Winchester, IN (US); Deborah Jones, Winchester, IN (US)

(72) Inventors: William Jones, Winchester, IN (US); Deborah Jones, Winchester, IN (US)

(*) Notice: Subject to any disclaimer, the term of this patent is extended or adjusted under 35 U.S.C. 154(b) by 347 days.

(21) Appl. No.: 15/949,173

(22) Filed: Apr. 10, 2018

(51) Int. Cl.
*A61F 7/00* (2006.01)
*A61H 11/00* (2006.01)
*A61F 7/02* (2006.01)

(52) U.S. Cl.
CPC ............ *A61F 7/0085* (2013.01); *A61F 7/02* (2013.01); *A61H 11/00* (2013.01); *A61F 2007/0029* (2013.01); *A61F 2007/0056* (2013.01); *A61F 2007/0076* (2013.01); *A61F 2007/0082* (2013.01); *A61F 2007/0086* (2013.01); *A61F 2007/0228* (2013.01); *A61F 2007/0231* (2013.01); *A61H 2011/005* (2013.01); *A61H 2201/0207* (2013.01); *A61H 2201/0214* (2013.01); *A61H 2201/0242* (2013.01);
(Continued)

(58) Field of Classification Search
CPC .......... A61F 7/00–123; A61F 2007/0001–126; A61F 7/02; A61F 7/0085; A61F 2007/0029; A61F 2007/0056; A61F 2007/0076; A61F 2007/0082; A61F 2007/0086; A61F 2007/0228; A61F 2007/0231; A61H 2201/165; A61H 2201/0207; A61H 2201/0214; A61H 2011/005; A61H 2011/0207; A61H 2011/0214; A61H 2011/0242; A61H 2011/0264; A61H 2011/10; A61H 2011/1652
See application file for complete search history.

(56) References Cited

U.S. PATENT DOCUMENTS 3,132,688 A    5/1964  Nowak
4,149,529 A *  4/1979  Copeland ............ A61H 9/0078
                                                          601/151
(Continued)

FOREIGN PATENT DOCUMENTS

WO    2007014242    7/2005

*Primary Examiner* — Samchuan C Yao
*Assistant Examiner* — Nathan M Le (57) ABSTRACT

The electronically regulated temperature compression device is a brace that applies pressure to an appendage. The electronically regulated temperature compression device applies heat therapy and cooling therapy to the appendage. The temperature of the selected therapy is electronically regulated and controlled. The electronically regulated temperature compression device uses a refrigerant-based heat exchange mechanism during the therapy process. The electronically regulated temperature compression device comprises a composite textile, plurality of fasteners, and a controller. The plurality of fasteners attaches the composite textile to the appendage of the patient. The plurality of fasteners controls the pressure applied by the composite textile to the appendage. The composite textile is a temperature controlled textile used to generate a heat exchange between the electronically regulated temperature compression device and the appendage. The controller manages the temperature and flow of the refrigerant during the therapy process.

17 Claims, 6 Drawing Sheets

(52) U.S. Cl.
CPC .. *A61H 2201/0264* (2013.01); *A61H 2201/10* (2013.01); *A61H 2201/1652* (2013.01)

(56) References Cited

U.S. PATENT DOCUMENTS

| | | | | |
|---|---|---|---|---|
| 4,335,726 A | * | 6/1982 | Kolstedt | A61F 7/10 607/104 |
| 4,998,415 A | * | 3/1991 | Larsen | A41D 13/0053 62/231 |
| 5,190,032 A | | 3/1993 | Zacoi | |
| 5,411,541 A | * | 5/1995 | Bell | A61F 7/02 601/15 |
| D383,546 S | | 9/1997 | Amis | |
| 5,902,256 A | * | 5/1999 | Benaron | A61H 23/0263 601/108 |
| 6,254,554 B1 | * | 7/2001 | Turtzo | A61H 9/0078 601/134 |
| 7,744,551 B2 | | 6/2010 | Pick | |
| 8,425,579 B1 | | 4/2013 | Edelman | |
| 8,603,151 B2 | * | 12/2013 | Latham | A61F 7/00 607/112 |
| 2004/0210176 A1 | * | 10/2004 | Diana | A61H 9/0078 601/151 |
| 2005/0075593 A1 | * | 4/2005 | Smith | A61F 5/028 602/2 |
| 2012/0283607 A1 | * | 11/2012 | Batra | A61F 7/02 601/18 |
| 2013/0233531 A1 | * | 9/2013 | Chiu | A61F 7/0085 165/281 |

\* cited by examiner

ELECTRONICALLY REGULATED TEMPERATURE COMPRESSION BRACE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary devices including therapeutic devices incorporating heating and cooling devices, more specifically, a compress with an electronically regulated mechanism for generating and applying heated and cooled fluids.

SUMMARY OF INVENTION

The electronically regulated temperature compression device is a therapeutic device. The electronically regulated temperature compression device is configured for use with a patient. The patient is further defined with an appendage. The electronically regulated temperature compression device is a brace that is placed around the appendage. The pressure of the electronically regulated temperature compression device against the appendage is adjustable. The electronically regulated temperature compression device is a thermal device. The electronically regulated temperature compression device can be used to apply to the appendage a therapy selected from the group consisting of a heating therapy and a cooling therapy. The temperature of the selected therapy is electronically regulated and controlled. The electronically regulated temperature compression device uses a refrigerant-based heat exchange mechanism during the therapy process. The electronically regulated temperature compression device comprises a composite textile, a plurality of fasteners, and a controller. The plurality of fasteners attach the composite textile to the appendage of the patient. The plurality of fasteners controls the pressure applied by the composite textile to the appendage. The composite textile is a temperature controlled textile used to generate a heat exchange between the electronically regulated temperature compression device and the appendage. The controller manages the temperature and flow of the refrigerant during the therapy process.

These together with additional objects, features and advantages of the electronically regulated temperature compression device will be readily apparent to those of ordinary skill in the art upon reading the following detailed description of the presently preferred, but nonetheless illustrative, embodiments when taken in conjunction with the accompanying drawings.

In this respect, before explaining the current embodiments of the electronically regulated temperature compression device in detail, it is to be understood that the electronically regulated temperature compression device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the electronically regulated temperature compression device.

It is therefore important that the claims be regarded as including such equivalent construction insofar as they do not depart from the spirit and scope of the electronically regulated temperature compression device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 6.

The electronically regulated temperature compression device 100 (hereinafter invention) is a therapeutic device. The invention 100 is configured for use with a patient 291. The patient 291 is further defined with an appendage 292. The invention 100 is a brace that is placed around the appendage 292. The pressure of the invention 100 against the appendage 292 is adjustable. The invention 100 is a thermal device. The invention 100 applies to the appendage 292 a therapy selected from the group consisting of a heating therapy and a cooling therapy. The temperature of the selected therapy is electronically regulated and controlled. The invention 100 uses a refrigerant 165 based heat exchange mechanism during the therapy process. The invention 100 comprises a composite textile 101, a plurality of fasteners 102, and a controller 103. The plurality of fasteners 102 attach the composite textile 101 to the appendage 292 of the patient 291. The plurality of fasteners 102 controls the pressure applied by the composite textile 101 to the appendage 292. The composite textile 101 is a temperature controlled textile used to generate a heat exchange between the invention 100 and the appendage 292. The controller 103 manages the temperature and flow of the refrigerant 165 during the therapy process.

The composite textile 101 is a flexible structure. The composite textile 101 is a layered structure. The composite textile 101 wraps around the appendage 292 of the patient 291 to form the therapeutic brace. The composite textile 101 transports the refrigerant 165 around the appendage 292 of the patient 291 in order to apply a therapy to the appendage 292 selected from the group consisting of heat therapy and cold therapy. The composite textile 101 comprises an inner layer 111, an outer layer 112, and a hairpin exchanger 113.

The inner layer 111 is a commercially available sheeting. The inner layer 111 forms an exterior layer of the composite textile 101. The inner layer 111 is the layer of the composite textile 101 that is placed against the appendage 292 of the patient 291. The outer layer 112 is a commercially available sheeting. The outer layer 112 forms an exterior layer of the composite textile 101. The outer layer 112 is the layer of the composite textile 101 that is distal to the inner layer 111.

The hairpin exchanger 113 is a flexible structure. The hairpin exchanger 113 is a heat exchange device that transports the refrigerant 165 through the composite textile 101. The hairpin exchanger 113 is formed from a hose laid out in the hairpin exchanger 113 structure. The hairpin exchanger 113 is a fluid impermeable structure that transfers heat between the refrigerant 165 and the appendage 292 of the patient 291 for therapeutic purposes. The hairpin exchanger 113 forms an intermediate structure positioned between the inner layer 111 and the outer layer 112. The hairpin exchanger 113 is further defined elsewhere in this disclosure.

The inner layer 111, the outer layer 112, and the hairpin exchanger 113 are assembled using an adhesive.

The plurality of fasteners 102 forms a fastening device that attaches the composite textile 101 to the appendage 292 of the patient 291. Each of the plurality of fasteners 102 is adjustable such that the pressure applied to the appendage 292 of the patient 291 by the composite textile 101 is adjustable. The plurality of fasteners 102 comprises a collection of individual fasteners 121.

Each individual fastener 121 attaches the composite textile 101 to itself such that the composite textile 101 will form a loop around the appendage 292 of the patient 291. The individual fastener 121 adjusts such that the pressure applied to the appendage 292 of the patient 291 by the composite textile 101 will adjust. The individual fastener 121 is formed from commercially available components. In the first potential embodiment of the disclosure, each individual fastener 121 is identical. Each individual fastener 121 comprises an anchor point 122 and a hook and loop fastener 123.

The anchor point 122 is an attachment structure that is permanently attached to the composite textile 101. The hook and loop fastener 123 attaches to the anchor point 122.

Specifically, in the first potential embodiment of the disclosure, the hook and loop fastener 123 loops around the anchor point 122 to fasten: a) the hook and loop fastener 123 to itself; and b) to fasten the composite textile 101 to itself. The hook and loop fastener 123 is a commercially available base webbing that uses a hook and loop structure to attach to itself. The anchor point 122 comprises a D-ring 151 and an anchor webbing 152. The hook and loop fastener 123 further comprises a first hook/loop surface 153 and a second hook/loop surface 154.

The D-ring 151 is a commercially available ring. The hook and loop fastener 123 loops through and around the D-ring 151 to attach the composite textile 101 to itself. The anchor webbing 152 is a commercially available product that permanently attaches the D-ring 151 to the composite textile 101. Methods to use an anchor webbing 152 to attach a D-ring 151 to a composite textile 101 are well-known and documented in the textile and apparel arts.

The first hook/loop surface 153 is the element of the hook and loop fastener 123 that attaches to a first face of the base webbing that forms the hook and loop fastener 123. The second hook/loop surface 154 is the element of the hook and loop fastener 123 that attaches to a second face of the base webbing that forms the hook and loop fastener 123. The second face is distal from the first face. The hook and loop fastener 123, the first hook/loop surface 153, and the second hook/loop surface 154 are defined and described in greater detail elsewhere in this disclosure.

The plurality of fasteners 102 comprises a first fastener 131, a second fastener 132, a third fastener 133, and a fourth fastener 134. The first fastener 131 is an individual fastener 121 selected from the plurality of fasteners 102. The second fastener 132 is an individual fastener 121 selected from the plurality of fasteners 102. The third fastener 133 is an individual fastener 121 selected from the plurality of fasteners 102. The fourth fastener 134 is an individual fastener 121 selected from the plurality of fasteners 102. The first fastener 131 further comprises the first anchor point 201 and a first hook and loop fastener 211. The second fastener 132 further comprises the second anchor point 202 and a second hook and loop fastener 212. The third fastener 133 further comprises the third anchor point 203 and a third hook and loop fastener 213. The fourth fastener 134 further comprises the fourth anchor point 204 and a fourth hook and loop fastener 214.

The first anchor point 201 is the anchor point 122 associated with the first fastener 131. The second anchor point 202 is the anchor point 122 associated with the second fastener 132. The third anchor point 203 is the anchor point 122 associated with the third fastener 133. The fourth anchor point 204 is the anchor point 122 associated with the fourth fastener 134. The first hook and loop fastener 211 is the hook and loop fastener 123 associated with the first fastener 131. The second hook and loop fastener 212 is the hook and loop fastener 123 associated with the second fastener 132. The third hook and loop fastener 213 is the hook and loop fastener 123 associated with the third fastener 133. The fourth hook and loop fastener 214 is the hook and loop fastener 123 associated with the fourth fastener 134.

The controller 103 is an electromechanical device. The controller 103: a) pumps the refrigerant 165 through the composite textile 101 to supply the heat exchange medium required for the selected therapy; b) heats and cools the refrigerant 165 to a temperature appropriate for the selected therapy; and, c) maintains the refrigerant 165 at the temperature appropriate for the selected therapy. The controller 103 further comprises a cut off for safety purposes. Specifically, the controller 103 will cease operation after a predetermined amount of time. The controller 103 comprises a housing 141, a fluid management system 142, and a regulation system 143. The controller 103 is further defined with an electrical ground 248.

The housing 141 is a casing. The housing 141 contains the fluid management system 142 and the regulation system 143. The housing 141 is formed with all apertures and form factors necessary to allow the housing 141 to accommodate the use and operation of the invention 100.

The fluid management system 142 forms a fluidic cycle that performs the heat exchange functions required for the therapeutic processes provided by the composite textile 101. The fluid management system 142 is an electromechanical apparatus that: a) heats the refrigerant 165; b) cools the refrigerant 165; and, c) pumps the refrigerant 165 through the hairpin exchanger 113 of the composite textile 101. The fluid management system 142 comprises a reservoir 161, a pump 162, a fluid supply tube 163, a fluid return tube 164, and a refrigerant 165. The pump 162 is further defined with a fifteenth lead 245 and a sixteenth lead 246. The fifteenth lead 245 and the sixteenth lead 246 form the electrical power connections of the pump 162.

The reservoir 161 is a fluid impermeable containment structure that stores the refrigerant 165. The reservoir 161 is the location where the refrigerant 165 is heated and cooled. The pump 162 is a commercially available device. The pump 162 is a mechanical device that generates a pressure differential used for transporting the refrigerant 165 through the fluidic cycle formed by the hairpin exchanger 113 and the fluid management system 142 of the controller 103. The fluid supply tube 163 is a hose that transports the refrigerant 165 from the reservoir 161 to the hairpin exchanger 113. The fluid return tube 164 is a hose that transports the refrigerant 165 from the hairpin exchanger 113 to the reservoir 161 to complete the fluidic cycle of the fluid management system 142. The refrigerant 165 is a fluid used as a heat exchange medium for the therapeutic process.

The hairpin exchanger 113 further comprises a first fitting 181 and a second fitting 182. The first fitting 181 is a commercially available fitting that attaches the fluid supply tube 163 to the hairpin exchanger 113. The second fitting 182 is a commercially available fitting that attaches the fluid return tube 164 to the hairpin exchanger 113.

Figure 1:
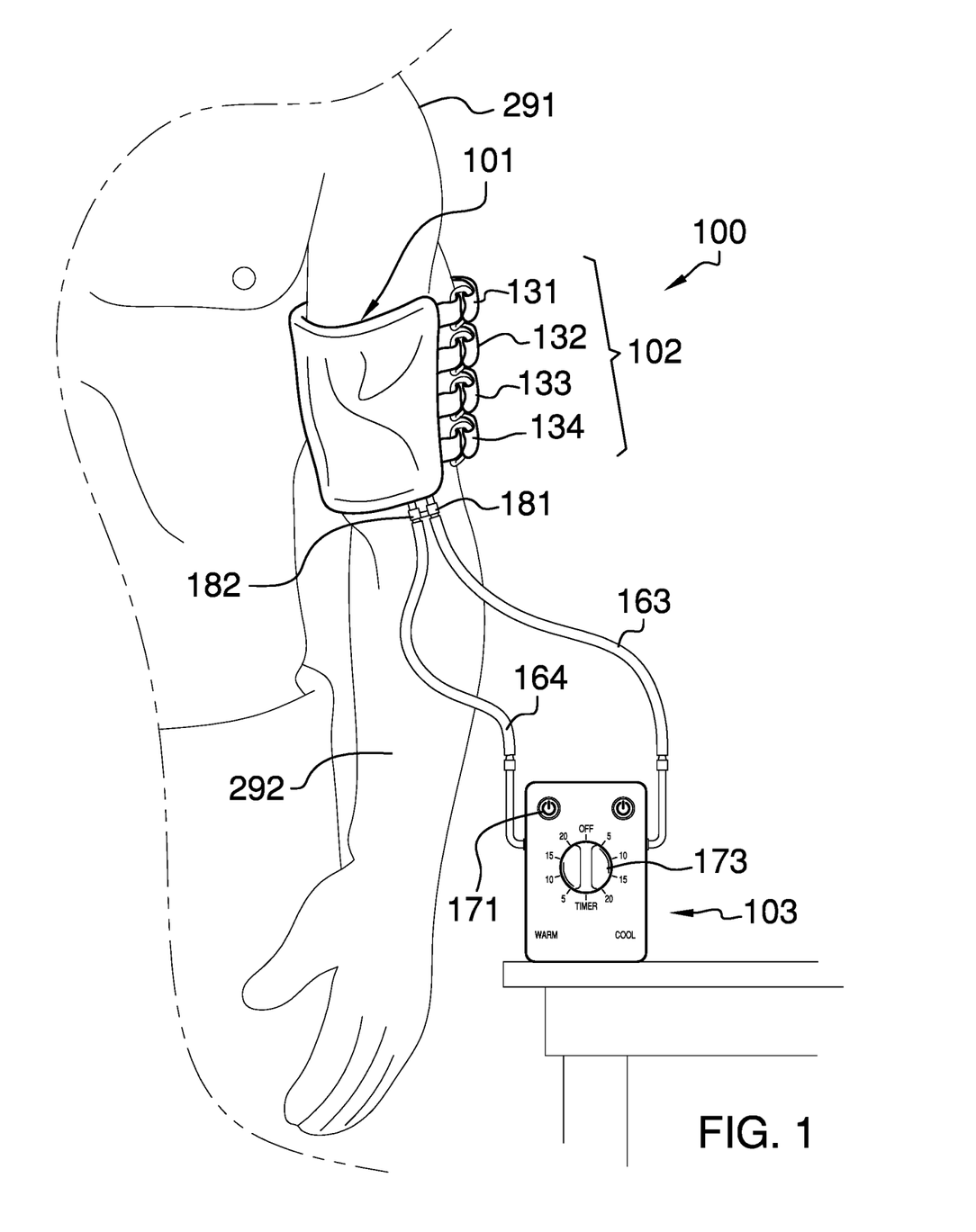
FIG. 1 is an in-use view of an embodiment of the disclosure.
Figure 2:
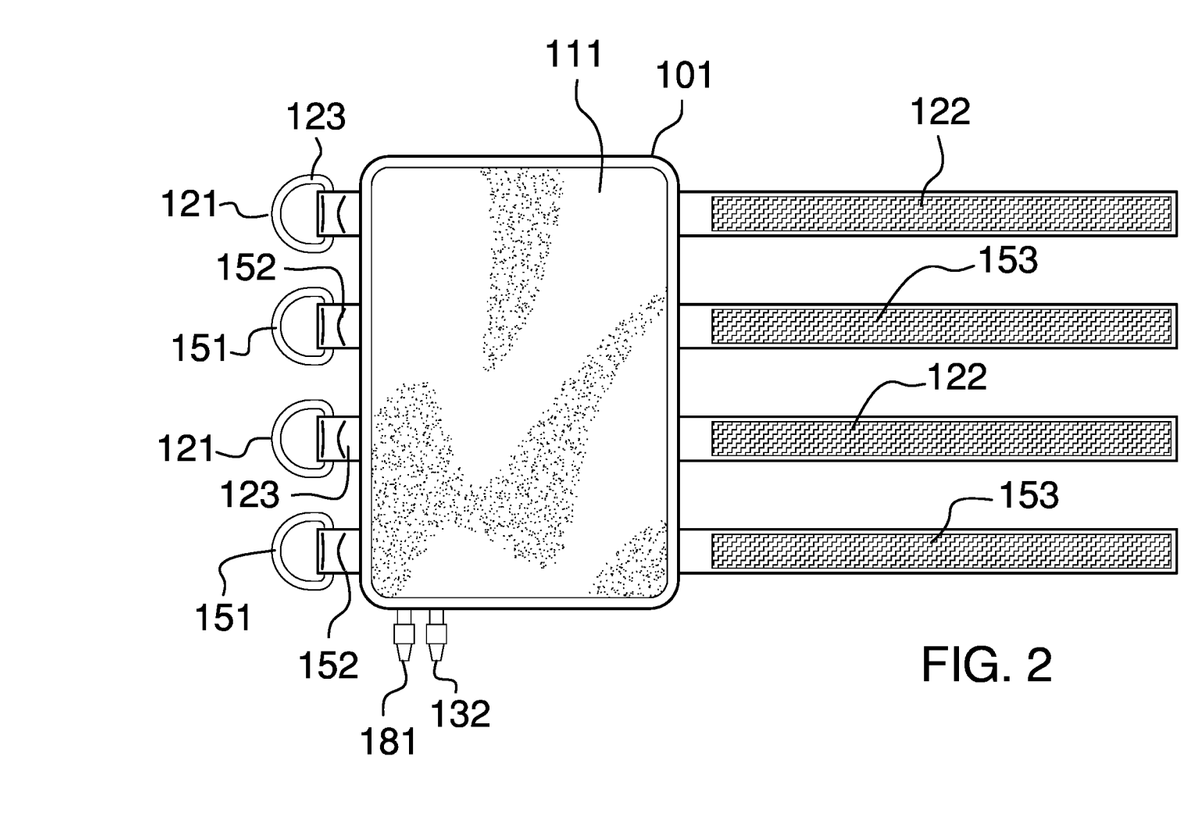
FIG. 2 is a bottom view of an embodiment of the disclosure.
Figure 3:
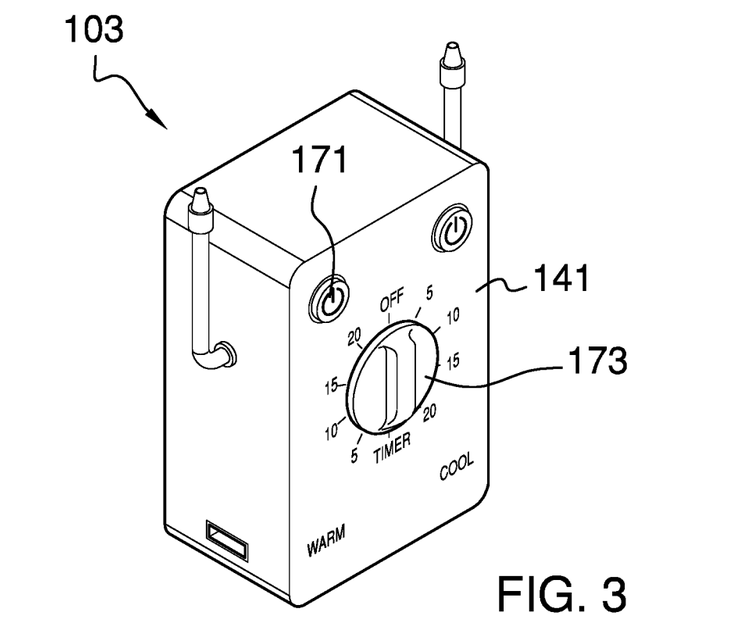
FIG. 3 is a perspective view of an embodiment of the disclosure.
Figure 4:
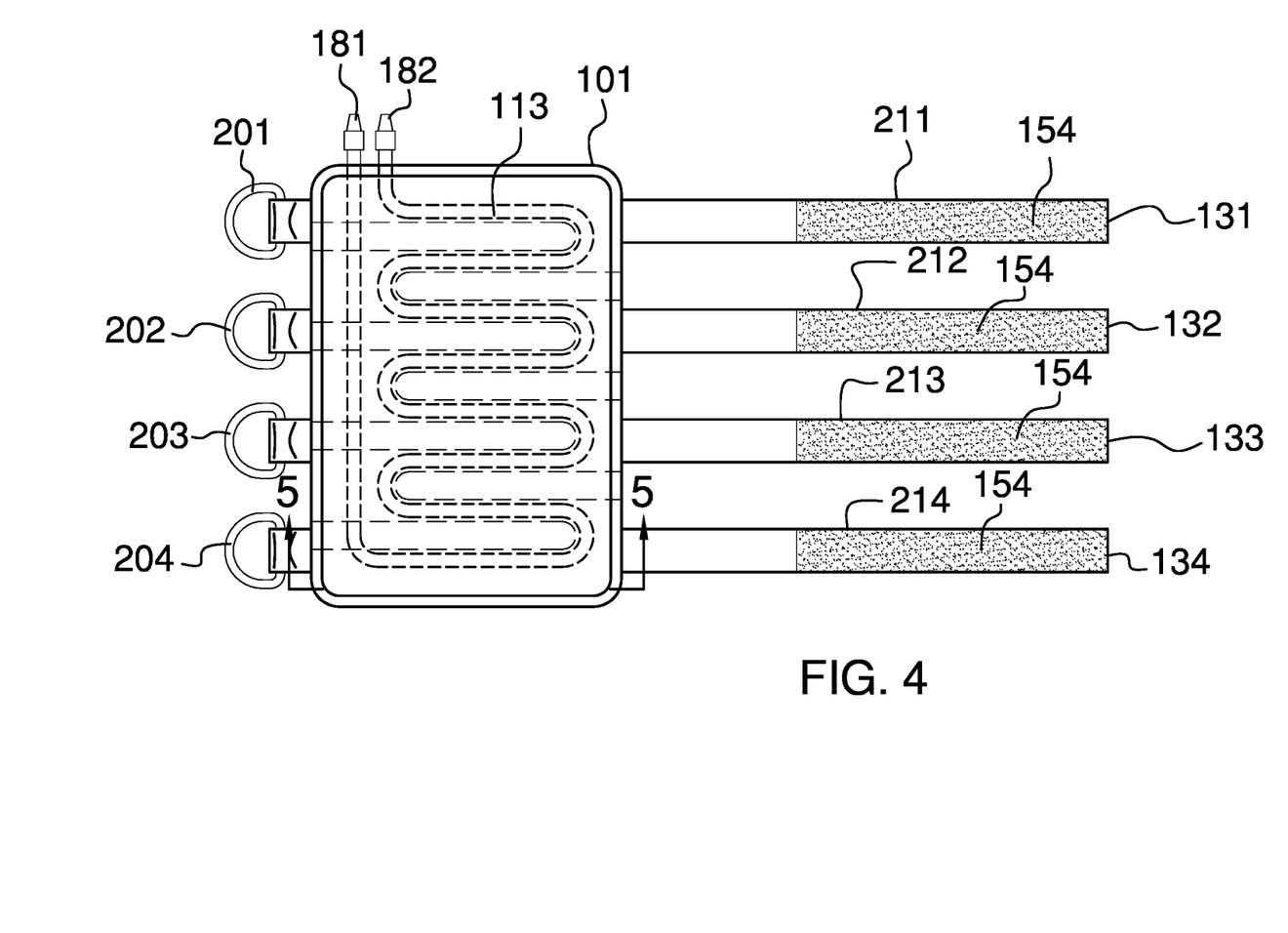
FIG. 4 is a top view of an embodiment of the disclosure.
Figure 5:
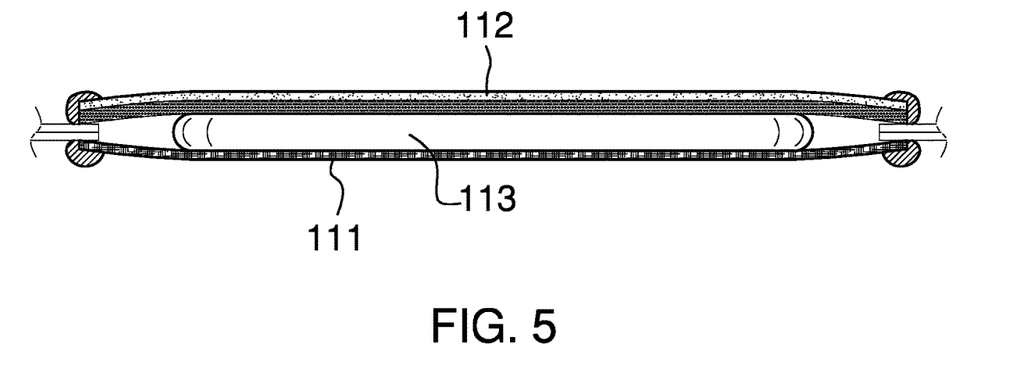
FIG. 5 is a cross-sectional view of an embodiment of the disclosure across 5-5 as shown in FIG. 4.
Figure 6:
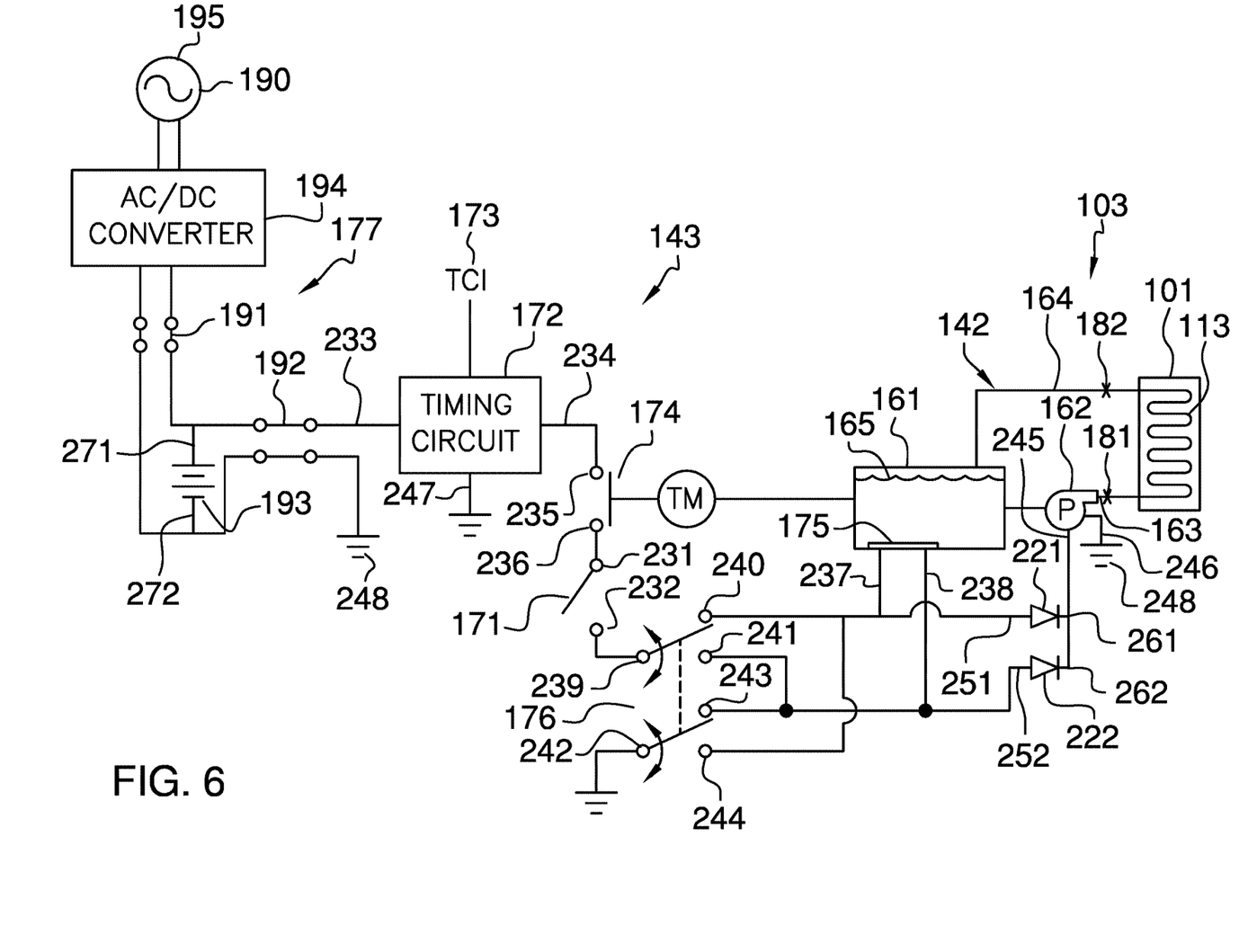
FIG. 6 is a block diagram of an embodiment of the disclosure.

The regulation system 143 is an electrical device that regulates and controls the operation of the fluid management system 142. The regulation system 143 provides the electrical power required for the operation of the fluid management system 142. The regulation system 143 uses a feedback mechanism to control the temperature of the refrigerant 165 during the operation of the invention 100. The regulation system 143 comprises a master switch 171, a timing circuit 172, a thermostat 174, a Peltier module 175, a double pole double throw switch 176, a power system 177, a first diode 221, and a second diode 222.

The master switch 171 is further defined with a first lead 231 and a second lead 232. The timing circuit 172 is further defined with a third lead 233, a fourth lead 234, and a seventeenth lead 247. The thermostat 174 is further defined with a fifth lead 235 and a sixth lead 236. The Peltier module 175 is further defined with a seventh lead 237 and an eighth lead 238. The double pole double throw switch 176 is further defined with a ninth lead 239, a tenth lead 240, an eleventh lead 241, a twelfth lead 242, a thirteenth lead 243 and a fourteenth lead 244. The first diode 221 is further defined with a first anode 251 and a first cathode 261. The second diode 222 is further defined with a second anode 252 and a second cathode 262. The master switch 171 is a commercially available maintained switch. The master switch 171 controls the flow of electricity through the controller 103. The master switch 171 is essentially the power switch of the invention 100.

The timing circuit 172 is an electrical circuit. The timing circuit 172 is a countdown timer. The timing circuit 172 limits the amount of time the controller 103 can operate by limiting the amount of time electric power can flow through the controller 103. The timing circuit 172 is defined and described in greater detail elsewhere in this disclosure. Methods to form a timing circuit 172 are well-known and documented in the electrical arts. The timing circuit interface 173 is a user interface device. The timing circuit interface 173 allows the patient 291 to adjust the countdown time of the timing circuit 172.

The thermostat 174 is a feedback device that controls the temperature of the refrigerant 165. The thermostat 174 is described in greater detail elsewhere in this disclosure. The use of a thermostat 174 is well-known and documented in the electrical arts.

The Peltier module 175 is an electrical device that can serve both as a heating element and a cooling element depending on the direction of the electric current flow through the Peltier module 175. The Peltier module 175 has two surfaces on opposite sides of the Peltier module 175. When electric current flows through the Peltier module 175, heat is transferred from one surface to the surface on the opposite side of the Peltier module 175. This creates a cold side and a warm side of the Peltier module 175 that is used as the cooling or heating elements of the invention 100. If the electric current flow through the Peltier device is reversed, the direction of heat transfer is reversed such that the cold and warm sides of the Peltier module 175 are also reversed.

The double pole double throw switch 176 is a commercially available double pole double throw switch 176. The double pole double throw switch 176 operates as a maintained switch. The double pole double throw switch 176 is used to select between a refrigerant 165 heating mode and a refrigerant 165 cooling mode during use of the invention 100. The operation of the double pole double throw switch 176 is described in greater detail elsewhere in this disclosure.

The first diode 221 is an electrical device that prevents the flow of electricity from the fifteenth lead 245 of the pump 162 to the tenth lead 240 of the double pole double throw switch 176. The second diode 222 is an electrical device that prevents the flow of electricity from the fifteenth lead 245 of the pump 162 to the thirteenth lead 243 of the double pole double throw switch 176.

The power system 177 is an electrical circuit that provides the electrical power necessary to operate the controller 103. The power system 177 comprises a first port/plug connection 191, a second port/plug connection 192, a battery 193, and an AC/DC converter 194. The AC/DC converter 194 is configured for use with the national electric grid 195. The battery 193 is further defined with a positive terminal 271 and a negative terminal 272.

The battery 193 is a commercially available chemical device that converts chemically stored energy into electrical energy. The first port/plug connection 191 is a modular electrical connector that electrically connects the battery 193 to the AC/DC converter 194 in a removable fashion. The use of the first port/plug connection 191 allows the controller 103 to be operated independently from an external electrical power source such as the national electric grid 195 by the battery 193. The second port/plug connection 192 is a modular electrical connector that electrically connects the battery 193 to the regulation system 143 in a removable fashion. The use of the second port/plug connection 192 allows a battery 193 that has been discharged from use with a charged second battery 193. The use of ports and plugs are well-known and documented in the electrical arts.

The AC/DC converter 194 is an electrical device that converts AC electric energy provided by the national electric grid 195 into DC electrical energy used to: a) recharge the battery 193; and, b) power the operation of the controller 103. The national electric grid 195 is described in greater detail elsewhere in this disclosure.

The following four paragraphs describe the assembly of the regulation system 143 of the controller 103.

The positive terminal 271 of the battery 193 electrically connects to the third lead 233 of the timing circuit 172 using the second port/plug connection 192. The fourth lead 234 of the timing circuit 172 electrically connects to the fifth lead 235 of the thermostat 174. The sixth lead 236 of the thermostat 174 electrically connects to the first lead 231 of the master switch 171. The second lead 232 of the master switch 171 electrically connects to the ninth lead 239 of the double pole double throw switch 176. The tenth lead 240 of the double pole double throw switch 176 electrically connects to the seventh lead 237 of the Peltier module 175.

The tenth lead 240 of the double pole double throw switch 176 electrically connects to the fourteenth lead 244 of the double pole double throw switch 176. The eleventh lead 241 of the double pole double throw switch 176 electrically connects to the thirteenth lead 243 of the double pole double throw switch 176. The thirteenth lead 243 of the double pole double throw switch 176 electrically connects to the eighth lead 238 of the Peltier module 175.

The tenth lead 240 of the double pole double throw switch 176 electrically connects to the first anode 251 of the first diode 221. The thirteenth lead 243 of the double pole double throw switch 176 electrically connects to the second anode 252 of the second diode 222. The first cathode 261 of the first diode 221 electrically connects to the fifteenth lead 245 of the pump 162. The second cathode 262 of the second diode 222 electrically connects to the fifteenth lead 245 of the pump 162.

The negative terminal 272 of the battery 193 electrically connects to the electrical ground 248 of the controller 103 using the second port/plug connection 192. The seventeenth lead 247 of the timing circuit 172 electrically connects to the electrical ground 248 of the controller 103. The twelfth lead 242 of the double pole double throw switch 176 electrically connects to the electrical ground 248 of the controller 103. The sixteenth lead 246 of the pump 162 electrically connects to the electrical ground 248 of the controller 103.

This paragraph describes the fluidic cycle formed by the fluid management system 142. The pump 162 draws refrigerant 165 from the reservoir 161. The pump 162 pumps the refrigerant 165 into the fluid supply tube 163. The first fitting 181 forms a fluidic connection between the fluid supply tube 163 and the intake of the hairpin exchanger 113. The second fitting 182 forms a fluidic connection between the hairpin exchanger 113 to the fluid return tube 164. The fluid return tube 164 forms a fluidic connection between the second fitting 182 and the reservoir 161 such that the refrigerant 165 returns to the reservoir 161 to complete the fluidic cycle of the fluid management system 142.

The following three paragraphs describe the operation of the double pole double throw switch 176.

The double pole double throw switch 176 forms a set of electrical connections selected from the group consisting of: a) a first electrical setting that electrically connects the ninth lead 239 to the tenth lead 240 while simultaneously connecting the twelfth lead 242 to the thirteenth lead 243; and, b) a second electrical setting that electrically connects the ninth lead 239 to the eleventh lead 241 while simultaneously connecting the twelfth lead 242 to the fourteenth lead 244.

In the first electrical setting electric power is routed: a) to the seventh lead 237 of the Peltier module 175; and, b) to the fifteenth lead 245 of the pump 162 through the first diode 221. The eighth lead 238 of the Peltier module 175 electrically connects to the electrical ground 248 of the controller 103 through the thirteenth lead 243 and the twelfth lead 242. The sixteenth lead 246 of the pump 162 electrically connects directly to the electrical ground 248 of the controller 103.

In the second electrical setting power is routed: a) to the eighth lead 238 of the Peltier module 175; and, b) to the fifteenth lead 245 of the pump 162 through the second diode 222. The seventh lead 237 of the Peltier module 175 electrically connects to the electrical ground 248 of the controller 103 through the fourteenth lead 244 and the twelfth lead 242. The sixteenth lead 246 of the pump 162 electrically connects directly to the electrical ground 248 of the controller 103.

The following definitions were used in this disclosure:

AC: As used in this disclosure, AC is an acronym for alternating current.

AC/DC Converter: As used in this disclosure, an AC/DC converter is an electrical device that converts an AC voltage into a regulated DC voltage by rectifying and regulating the AC voltage. Method to design and build AC/DC converters are well known in the electrical arts.

Anchor: As used in this disclosure, anchor means to hold an object firmly or securely.

Anchor Point: As used in this disclosure, an anchor point is a location to which a first object can be securely attached to a second object.

And/Or: As used in this disclosure, the term and/or is a grammatical conjunction that implies an inclusive or. Specifically, the term and/or implies that at least one and potentially more than one of the plurality of statements joined by the and/or conjunction will be true.

Appendage: As used in this disclosure, an appendage is a generic term used to describe either the arm and/or leg of a patient.

Battery: As used in this disclosure, a battery is a chemical device consisting of one or more cells, in which chemical energy is converted into electricity and used as a source of power. Batteries are commonly defined with a positive terminal and a negative terminal.

Composite Textile: As used in this disclosure, a composite textile is a multilayer fabric made of two or more joined layers of textile or sheeting materials.

DC: As used in this disclosure, DC is an acronym for direct current.

Diode: As used in this disclosure, a diode is a two terminal semiconductor device that allows current flow in only one direction. The two terminals are called the anode and the cathode. Electric current is allowed to pass from the anode to the cathode.

Electrical Ground: As used in this disclosure, an electrical ground is a common reference voltage used in the design and implementation of electrical circuits. An electrical ground is often, but not necessarily, the discharge point of electric currents flowing through an electric circuit.

Fastener: As used in this disclosure, a fastener is a device that is used to join or affix two objects. Fasteners generally comprise a first element which is attached to the first object and a second element which is attached to the second object such that the first element and the second element join to affix the first object and the second object. Common fasteners include, but are not limited to, hooks, zippers, magnets, snaps, buttons, buckles, quick release buckles, or hook and loop fasteners.

Feedback: As used in this disclosure, feedback refers to a system, including engineered systems, or a subsystem further comprising an "input" and an "output" wherein the difference between the output of the engineered system or subsystem and a reference is used as, or fed back into, a portion of the input of the system or subsystem. Examples of feedback in engineered systems include, but are not limited to, a fluid level control device such as those typically used in a toilet tank, a cruise control in an automobile, a fly ball governor, a thermostat, and almost any electronic device that comprises an amplifier. Feedback systems in nature include, but are not limited to, thermal regulation in animals and blood clotting in animals (wherein the platelets involved in blood clotting release chemical to attract other platelets)

Fitting: As used in this disclosure, a fitting is a component that is attached to a first object. The fitting is used to forming a fluidic connection between the first object and a second object.

Flexible: As used in this disclosure, flexible refers to an object or material that will deform when a force is applied to it but that will not necessarily return to its original shape when the deforming force is removed.

Fluid: As used in this disclosure, a fluid refers to a state of matter wherein the matter is capable of flow and takes the shape of a container it is placed within. The term fluid commonly refers to a liquid or a gas.

Fluidic Connection: As used in this disclosure, a fluidic connection refers to a tubular structure that transports a fluid from a first object to a second object. Methods to design and use a fluidic connection are well-known and documented in the mechanical, chemical, and plumbing arts.

Form Factor: As used in this disclosure, the term form factor refers to the size and shape of an object.

Hairpin Exchanger: As used in this disclosure, a hairpin exchanger is a heat exchange structure formed a plurality of straight tubes connected using a hairpin tube.

Hairpin Tube: As used in this disclosure, a hairpin tube is a tube or pipe structure wherein tube or pipe is bent in a "U" shape reminiscent of a hairpin turn. This "U" reverses the actual physical direction of fluid flow while maintaining the direction of the fluid flow through the tube. Hairpin tube structures are often used in heat exchangers.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook/loop surface" with the understanding that when the two objects are fastened together one of the two objects will have a hook surface and the remaining object will have the loop surface.

Hose: As used in this disclosure, a hose is a flexible hollow cylindrical device used for transporting liquids and gases. When referring to a hose in this disclosure, the terms inner diameter and outer diameter are used as they would be used by those skilled in the plumbing arts.

Housing: As used in this disclosure, a housing is a rigid casing that encloses and protects one or more devices.

Interface: As used in this disclosure, an interface is a physical or virtual boundary that separates two different systems across which information is exchanged.

Intermediate: As used in this disclosure, the term intermediate refers to a location that lies between a first object and a second object Loop: As used in this disclosure, a loop is the length of a first linear structure including, but not limited to, shafts, lines, cords, or ribbons, that is: 1) folded over and joined at the ends forming an enclosed space; or, 2) curved to form a closed or nearly closed space within the first linear structure. In both cases, the space formed within the first linear structure is such that a second linear structure such as a line, cord or a hook can be inserted through the space formed within the first linear structure. Within this disclosure, the first linear structure is said to be looped around the second linear structure.

Maintained Switch: A used in this disclosure, a maintained switch is a switch that maintains the position that was set in the most recent switch actuation. A maintained switch works in an opposite manner to a momentary switch.

National Electric Grid: As used in this disclosure, the national electric grid is a synchronized and highly interconnected electrical network that distributes energy in the form of electric power from a plurality of generating stations to consumers of electricity.

Patient: As used in this disclosure, a patient is a person who is designated to receive a medical treatment, therapy or service. The term patient may be extended to an animal when used within the context of the animal receiving veterinary treatment or services Peltier Module: As used in this disclosure, a Peltier module refers to a flat solid-state device that uses the Peltier thermoelectric effect to create a warm side of the device and a cool side of the device. The side of the device that is warm and the side of the device that is cool can be reversed by reversing the current flow through the device.

Plug: As used in this disclosure, a plug is an electrical termination that electrically connects a first electrical circuit to a second electrical circuit or a source of electricity. As used in this disclosure, a plug will have two or three metal pins.

Port: As used in this disclosure, a port is an electrical termination that is used to connect a first electrical circuit to a second external electrical circuit. In this disclosure, the port is designed to receive a plug.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Pump: As used in this disclosure, a pump is a mechanical device that uses suction or pressure to raise or move fluids, compress fluids, or force a fluid into an inflatable object. Within this disclosure, a compressor refers to a pump dedicated to compressing a fluid or placing a fluid under pressure.

Refrigerant: As used in this disclosure, a refrigerant is a fluid used as the heat exchange medium in a heat exchange system.

Reservoir: As used in this disclosure, a reservoir refers to a container or containment system that is configured to store a liquid.

Ring: As used in this disclosure, a ring is a term that is used to describe a flat or plate-like structure through which an aperture is formed.

Sheeting: As used in this disclosure, a sheeting is a material, such as a textile, a plastic, or a metal foil, in the form of a thin flexible layer or layers.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Textile: As used in this disclosure, a textile is a material that is woven, knitted, braided or felted. Synonyms in common usage for this definition include fabric and cloth.

Therapeutic: As used in this disclosure, therapeutic is an adjective that refers to a medical, ameliorative, or hygienic substance, process, or procedure.

Thermostat: As used in this disclosure, a thermostat is a device that monitors the temperature of a space such that the thermostat 1) operates a switch when the measured temperature exceeds or falls below a first preset temperature; and, 2) performs the opposite operation on the switch when the measured temperature falls below or exceeds a second preset temperature.

Timing Circuit: As used in this disclosure, a timing circuit refers to an electrical network of interconnected electrical elements, potentially including but not limited to, resistors, capacitors, diodes, transistors, and integrated circuit devices. The purpose of the timing circuit is to generate an electrical control signal after a predetermined amount of time. In common usage, a timing circuit is also referred to as timing circuitry. The "555" timing circuit is a well-known, documented, and commercially available timing circuit.

Tube: As used in this disclosure, a tube is a hollow prism-shaped device formed with two open ends. The tube is used for transporting liquids and gases. The line that connects the center of the first congruent face of the prism to the center of the second congruent face of the prism is referred to as the center axis of the tube or the centerline of the tube. When two tubes share the same centerline they are said to be aligned. When the centerlines of two tubes are perpendicular to each other, the tubes are said to be perpendicular to each other. In this disclosure, the terms inner dimensions of a tube and outer dimensions of a tube are used as they would be used by those skilled in the plumbing arts.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips. Webbings have tensile strength but are too flexible to provide compressive strength and are not suitable for use in pushing objects.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A therapeutic device comprising
a composite textile, a plurality of fasteners, and a controller;
wherein the plurality of fasteners is configured to attach the composite textile to an appendage of a patient;
wherein the composite textile is a temperature controlled textile used to generate a heat exchange between the therapeutic device and the appendage;
wherein the therapeutic device is configured to be placed around the appendage;
wherein the pressure of the therapeutic device against the appendage is adjustable;
wherein the therapeutic device is a thermal device;
wherein the therapeutic device applies to the appendage a therapy process selected from the group consisting of a heating therapy and a cooling therapy;
wherein the plurality of fasteners control the pressure applied by the composite textile to the appendage;
wherein the temperature of the selected therapy is regulated and controlled;
wherein the therapeutic device uses a refrigerant based heat exchange mechanism during the selected therapy process;
wherein the controller manages the temperature and flow of the refrigerant during the therapy process;
wherein the controller comprises a housing, a fluid management system, and a regulation system;
wherein the regulation system comprises a master switch, a timing circuit, a thermostat, a Peltier module, a double pole double throw switch, a power system, a first diode, and a second diode;
wherein the master switch controls the flow of electricity through the controller;
wherein the timing circuit is an electrical circuit;
wherein the timing circuit is a countdown timer;
wherein the timing circuit limits the amount of time the controller can operate by limiting the amount of time electric power can flow through the controller;
wherein the thermostat is a feedback device;

wherein the thermostat controls the temperature of the refrigerant;
wherein the Peltier module is an electrical device that heats the refrigerant;
wherein the Peltier module is an electrical device that cools the refrigerant;
wherein the double pole double throw switch is a pole double throw switch;
wherein the double pole double throw switch selects between a refrigerant heating mode and a refrigerant cooling mode;
wherein the first diode is an electrical device that prevents the flow of electricity from a first lead of the pump to a first lead of the double pole double throw switch;
wherein the second diode is an electrical device that prevents the flow of electricity from the first lead of the pump to a second lead of the double pole double throw switch.

2. The therapeutic device according to claim 1
wherein the composite textile is a flexible structure;
wherein the composite textile is a layered structure;
wherein the composite textile wraps around the appendage of the patient;
wherein the composite textile transports the refrigerant around the appendage of the patient.

3. The therapeutic device according to claim 2
wherein the plurality of fasteners form a fastening device that attaches the composite textile to the appendage of the patient;
wherein each of the plurality of fasteners is adjustable;
wherein the plurality of fasteners comprise a collection of individual fasteners;
wherein each individual fastener attaches the composite textile to itself such that the composite textile will form a loop around the appendage of the patient;
wherein the individual fastener adjusts such that the pressure applied to the appendage of the patient by the composite textile will adjust.

4. The therapeutic device according to claim 3
wherein the controller is an electromechanical device;
wherein the controller pumps the refrigerant through the composite textile;
wherein the controller heats and cools the refrigerant;
wherein the controller will cease operation after a predetermined amount of time.

5. The therapeutic device according to claim 4
wherein the composite textile comprises an inner layer, an outer layer, and a hairpin exchanger;
wherein the inner layer is a sheeting;
wherein the outer layer is a sheeting;
wherein the hairpin exchanger forms an intermediate structure positioned between the inner layer and the outer layer.

6. The therapeutic device according to claim 5
wherein the hairpin exchanger is a heat exchange device that transports the refrigerant through the composite textile;
wherein the hairpin exchanger transfers energy between the refrigerant and the appendage of the patient for therapeutic purposes.

7. The therapeutic device according to claim 6
wherein the hairpin exchanger is a flexible structure;
wherein the hairpin exchanger is a fluid impermeable structure;
wherein the hairpin exchanger is formed from a hose.

8. The therapeutic device according to claim 7
wherein each individual fastener comprises an anchor point and a hook and loop fastener;
wherein the anchor point is an attachment structure;
wherein the anchor point is permanently attached to the composite textile;
wherein the hook and loop fastener attaches to the anchor point;
wherein the hook and loop fastener uses a hook and loop structure to attach to itself.

9. The therapeutic device according to claim 8
wherein the anchor point comprises a D-ring and an anchor webbing;
wherein the anchor webbing permanently attaches the D-ring to the composite textile;
wherein the hook and loop fastener further comprises a first hook/loop surface and a second hook/loop surface;
wherein the D-ring is a ring;
wherein the hook and loop fastener loops through and around the D-ring to attach the composite textile to itself.

10. The therapeutic device according to claim 9
wherein the fluid management system forms a fluidic cycle that performs the heat exchange functions required for the selected therapy process;
wherein the regulation system is an electrical device that regulates and controls the operation of the fluid management system;
wherein the controller is further defined with an electrical ground;
wherein the housing is a casing;
wherein the housing contains the fluid management system and the regulation system.

11. The therapeutic device according to claim 10
wherein the fluid management system is an electromechanical apparatus that heats the refrigerant;
wherein the fluid management system cools the refrigerant;
wherein the fluid management system pumps the refrigerant through the hairpin exchanger of the composite textile;
wherein the regulation system provides the electrical power required for the operation of the fluid management system;
wherein the regulation system is a feedback mechanism that controls the temperature of the refrigerant during the operation of the therapeutic device.

12. The therapeutic device according to claim 11
wherein the fluid management system comprises a reservoir, a pump, a fluid supply tube, a fluid return tube, and the refrigerant;
wherein the reservoir, the pump, the fluid supply tube, the fluid return tube, and the refrigerant are fluidically interconnected;
wherein the pump is further defined with the first lead and a second lead;
wherein the first lead forms an electrical power connection of the pump;
wherein the second lead forms an electrical power connection of the pump.

13. The therapeutic device according to claim 12 wherein the reservoir is a fluid impermeable containment structure;
wherein the reservoir stores the refrigerant;
wherein the refrigerant is heated and cooled in the reservoir;
wherein the pump is a mechanical device that generates a pressure differential;

wherein the fluid supply tube transports the refrigerant from the reservoir to the hairpin exchanger;
wherein the fluid return tube is a hose that transports the refrigerant from the hairpin exchanger to the reservoir;
wherein the refrigerant is a fluid used as a heat exchange medium.

14. The therapeutic device according to claim 13
wherein the master switch, the timing circuit, the thermostat, the Peltier module, the double pole double throw switch, the power system, the first diode, and the second diode are electrically interconnected;
wherein the power system is an electrical circuit that provides the electrical power necessary to operate the controller;
wherein the master switch is further defined with a first lead and a second lead;
wherein the timing circuit is further defined with a third lead, a fourth lead, and a seventeenth lead;
wherein the thermostat is further defined with a fifth lead and a sixth lead;
wherein the Peltier module is further defined with a seventh lead and an eighth lead;
wherein the double pole double throw switch is further defined with the first lead, the second lead, a third lead, a fourth lead, a fifth lead, and a sixth lead;
wherein the first diode is further defined with a first anode and a first cathode;
wherein the second diode is further defined with a second anode and a second cathode.

15. The therapeutic device according to claim 14
wherein the power system comprises a first port/plug connection, a second port/plug connection, a battery, and an AC/DC converter;
wherein the battery is further defined with a positive terminal and a negative terminal;
wherein the AC/DC converter is configured for use with a national electric grid;
wherein the AC/DC converter is an electrical device that converts AC electric energy provided by the national electric grid into DC electrical energy;
wherein the battery converts chemically stored energy into electrical energy;
wherein the first port/plug connection is a modular electrical connector that electrically connects the battery to the AC/DC converter in a removable fashion;
wherein the second port/plug connection is a modular electrical connector that electrically connects the battery to the regulation system in a removable fashion.

16. The therapeutic device according to claim 15 wherein the hairpin exchanger further comprises a first fitting and a second fitting;
wherein the first fitting is a fitting that attaches the fluid supply tube to the hairpin exchanger;
wherein the second fitting is a fitting that attaches the fluid return tube to the hairpin exchanger;
wherein the pump draws the refrigerant from the reservoir;
wherein the pump pumps the refrigerant into the fluid supply tube;
wherein the first fitting forms a fluidic connection between the fluid supply tube and an intake of the hairpin exchanger;
wherein the second fitting forms a fluidic connection between the hairpin exchanger to the fluid return tube;
wherein the fluid return tube forms a fluidic connection between the second fitting and the reservoir such that the refrigerant returns to the reservoir to complete the fluidic cycle of the fluid management system.

17. The therapeutic device according to claim 16
wherein the plurality of fasteners comprise a first fastener, a second fastener, a third fastener, and a fourth fastener;
wherein the first fastener further comprises the first anchor point and a first hook and loop fastener;
wherein the second fastener further comprises the second anchor point and a second hook and loop fastener;
wherein the third fastener further comprises the third anchor point and a third hook and loop fastener;
wherein the fourth fastener further comprises the fourth anchor point and a fourth hook and loop fastener;
wherein the first anchor point is the anchor point associated with the first fastener;
wherein the second anchor point is the anchor point associated with the second fastener;
wherein the third anchor point is the anchor point associated with the third fastener;
wherein the fourth anchor point is the anchor point associated with the fourth fastener;
wherein the first hook and loop fastener is the hook and loop fastener associated with the first fastener;
wherein the second hook and loop fastener is the hook and loop fastener associated with the second fastener;
wherein the third hook and loop fastener is the hook and loop fastener associated with the third fastener;
wherein the fourth hook and loop fastener is the hook and loop fastener associated with the fourth fastener.

* * * * *